(12) United States Patent
Corma et al.

(10) Patent No.: US 7,087,793 B2
(45) Date of Patent: Aug. 8, 2006

(54) PROCESS FOR PRODUCING CYCLOALKANOL AND/OR CYCLOALKANONE

(75) Inventors: Avelino Corma, Valencia (ES); Jose Manuel Lopez Nieto, Paterna (ES)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/211,689

(22) Filed: Aug. 26, 2005

(65) Prior Publication Data

US 2006/0058556 A1 Mar. 16, 2006

(30) Foreign Application Priority Data

Sep. 3, 2004 (JP) ............................. 2004-256677

(51) Int. Cl.
*C07C 45/00* (2006.01)
(52) U.S. Cl. .................. 568/344; 568/375; 568/821; 568/836
(58) Field of Classification Search ................. None
See application file for complete search history.

(56) References Cited

U.S. PATENT DOCUMENTS

| 4,859,798 | A |  | 8/1989 | Lyons et al. |
| 5,817,881 | A |  | 10/1998 | Ellis et al. |
| 6,528,658 | B1 | * | 3/2003 | Miura et al. ................. 548/466 |
| 6,642,419 | B1 | * | 11/2003 | Miura et al. ................. 568/357 |
| 6,927,311 | B1 | * | 8/2005 | Tani et al. ................... 568/836 |

FOREIGN PATENT DOCUMENTS

| JP |  | 07-309793 | A |  | 11/1995 |
| JP |  | 2000-319211 | A |  | 11/2000 |
| JP |  | 1074536 | A1 | * | 2/2001 |
| JP |  | 2003-261484 | A |  | 9/2003 |

OTHER PUBLICATIONS

Nozaki et al. Oxidation of Cyclohexane with Molecular Oxygen Efficiently Catalyzed by Di-Iron(III)-Substituted Silicotungstate, gamma-SiW10 [Fe(OH2)]2 O38, Including Radical-Chain Mechanism. Cheimistry Letters, 1998, p. 1263-1264.*

Patent Abstracts of Japan, vol. 2003, No. 12, Dec. 5, 2003, corresponds to (JP 2003-261484).

* cited by examiner

*Primary Examiner*—Sikarl A. Witherspoon
(74) *Attorney, Agent, or Firm*—Sughrue Mion, PLLC

(57) ABSTRACT

The present invention provides a process for producing cycloalkanol and/or cycloalkanone by oxidizing cycloalkane with molecular oxygen in the presence of a heteropolyacid compound comprising a cobalt atom as a central element and a cobalt atom as a frame element.

6 Claims, No Drawings

PROCESS FOR PRODUCING CYCLOALKANOL AND/OR CYCLOALKANONE

BACKGROUND OF THE INVENTION

1. Field of the Invention

The invention relates to a method for producing cycloalkanol and/or cycloalkanone by oxidation of cycloalkane with molecular oxygen.

2. Description of the Related Art

As a method for producing cycloalkanol and/or cycloalkanone by oxidizing cycloalkane with molecular oxygen, a method using a heteropolyacid compound as a catalyst has been known in the art. For example, Chemistry Letters, p1263–1264, 1998 discloses use of an iron-substituted silicotungstates as a catalyst in which 1 to 3 tungsten atoms are substituted with iron atoms. Further, Japanese Patent Application Laid-Open No. 2000-319211 discloses use of a transition metal-substituted heteropolyacid compound as a catalyst in which at least two frame elements are substituted with IV to XI group elements other than iron. In addition, Japanese Patent Application Laid-Open No. 2003-261484 discloses use of a ruthenium-substituted silicotungstic acid compound as a catalyst in which one tungsten atom is substituted with a ruthenium atom.

SUMMARY OF THE INVENTION

The conventional methods, by which a high selectivity may be achieved, are not satisfactory in some cases from the view point of productivity, since the activity of the catalyst, which can be evaluated from the conversion of cycloalkane, is not always sufficient.

Accordingly, one of objects of the invention is to provide a process for producing cycloalkanol and/or cycloalkanone with a sufficient selectivity by oxidizing cycloalkane with a high conversion.

The present invention provides a process for producing cycloalkanol and/or cycloalkanone by oxidizing cycloalkane with molecular oxygen in the presence of a heteropolyacid compound comprising a cobalt atom as a central element and a cobalt atom as a frame element.

In accordance with the present invention, cycloalkane is oxidized with a high conversion to produce cycloalkanol and/or cycloalkanone with a high selectivity.

DETAILED DESCRIPTION OF THE PREFERRED EMBODIMENT

In the present invention, cycloalkane is used as a starting material, which is oxidized with molecular oxygen in the presence of a heteropolyacid compound to produce corresponding cycloalkanol and/or cycloalkane.

Examples of the cycloalkane as the starting material include monocyclic cycloalkane having no substituent on its ring such as cyclopropane, cyclobutane, cyclopentane, cyclohexane, cycloheptane, cyclooctane, cyclodecane and cyclooctadecane; polycyclic cycloalkane such as decalin and adamantane; and cycloalkane having a substituent on its ring such as methyl cyclopentane and methyl cyclohexane; and the like. Number of carbon atoms included in the cycloalkane is usually about 3 to 20. At least two of cycloalkanes may be used, if necessary.

An oxygen-containing gas may be used as a source of the molecular oxygen. The oxygen-containing gas may be, for example, air or pure oxygen, or may be diluted air or pure oxygen with an inert gas such as nitrogen, argon and helium. An oxygen-enriched air prepared by adding pure oxygen to air may be also used as the oxygen-containing gas.

In the present invention, a heteropolyacid compound comprising a cobalt atom as a central element and a cobalt atom as a frame element is used as a catalyst for oxidizing cycloalkane with molecular oxygen. By using the heteropolyacid catalyst, cycloalkane is oxidized with a high conversion, while cycloalkanol and/or cycloalkanone is produced with a sufficient selectivity. The central element herein is an element at the center of a condensed structure of the acid constituting the frame, and may be called as a hetero element. The frame element herein is an element forming, together with oxygen, the condensed structure of the acid, and the frame element may be called as a poly-element. Examples of the typical heteropolyacid structure include a Keggin structure having an atomic ratio of the central element/the frame element of 1/12, an Anderson structure having the atomic ratio of 1/6, and a Dawson structure having the atomic ratio of 2/18.

Preferably, the number of the cobalt atom included as the frame element is about 1 to 3 per one molecule. The frame element other than cobalt may be preferably tungsten or molybdenum. An element other than cobalt, tungsten and molybdenum may be included as the frame element, if necessary, and the number thereof may be about 3 per one molecule at most.

The heteropolyacid compound preferably has a heteropolyacid anion whose composition is represented by formula (1) below:

$$CoX_{11}CoO_{39} \tag{1}$$

wherein Co represents a cobalt atom, X represents a tungsten and/or molybdenum atom, and O represents an oxygen atom.

The heteropolyacid compound may be in the form of a free heteropolyacid or a salt of heteropolyacid, it is preferably a salt of heteropolyacid. The salt may be an acidic salt prepared by neutralizing a part of protons in the heteropolyacid, or may be a normal salt prepared by neutralizing all the protons in the heteropolyacid. Examples of a counter-cation of the heteropolyacid anion in the heteropolyacid compound include a cation of alkali metal such as lithium, sodium, potassium and cesium; a cation of alkali earth metal such as calcium and magnesium; an ammonium cation; a tetraalkylammonium cation with alkyl groups whose carbon numbers are about 1 to 20 respectively; and proton. At least two of counter-cations may be included, if necessary.

The heteropolyacid compound may be prepared by a well-known method, for example, by the method described in Journal of American Chemical Society, 1990, Vol. 112, p6025. Compounds containing the elements included in the heteropolyacid compounds described above, for example, oxo-acids, oxo-acid salts, oxides, nitrates, carbonates, hydroxides and halides, are used as the starting materials for preparing the compound in a proportion that satisfies a desired atomic ratio. Examples of the compound containing cobalt include cobalt acetate, cobalt chloride and cobalt oxide; examples of the compound containing tungsten include tungstic acid, tungstate and tungsten oxide; and examples of the compound containing molybdenum include molybdic acid, molybdate and molybdenum oxide.

The heteropolyacid compound may be used for oxidation reaction after being molded or being supported on a carrier such as silica, almina, titania, montmorillonite, zeolite and a hydrotalcite-like compound, if necessary. The heteropolyacid compound is preferably used with being supported on the hydrotalcite-like compound.

The hydrotalcite-like compound is a compound having a layer structure similar to that of hydrotalcite [$Mg_6Al_2(OH)_{16}CO_3 \cdot 4H_2O$], or a layered compound comprising anions between positively charged layers composed of divalent and trivalent metals. Examples of the layered compound include typically a compound in which the divalent metal is magnesium, the trivalent metal is aluminum, and interlayer anion is a carbonate ion (hydrotalcite), as well as a compound in which the divalent metal is zinc, the trivalent metal is aluminum, and an interlayer anion is a nitrate ion.

When the heteropolyacid compound is used with being supported on the carrier as a supported catalyst, the supported amount of total cobalt may be 0.01 to 4 parts by weight, preferably 0.1 to 2 parts by weight, with respect to 100 parts by weight of the entire supported catalyst, that is, the sum of the heteropolyacid compound and the carrier. The heteropolyacid compound may be subjected to pretreatment such as reduction treatment and calcination treatment, if necessary, before being utilized for reactions.

The oxidation reaction can be performed by allowing molecular oxygen to contact cycloalkane in the presence of the heteropolyacid compound. The amount of use of the heteropolyacid compound may be 0.001 to 10 parts by weight, preferably 0.01 to 5 parts by weight, with respect to 100 parts by weight of cycloalkane when the heteropolyacid compound is used without being supported on the carrier. When the heteropolyacid compound is used with being supported on the carrier, the amount of use thereof may be 0.01 to 50 parts by weight, preferably 0.1 to 10 parts by weight, with respect to 100 parts by weight of cycloalkane in terms of the entire supported catalyst, that is, the sum of the heteropolyacid compound and the carrier.

The oxidation reaction temperature may be 0 to 170° C., preferably 50 to 150° C., and the reaction pressure may be 0.1 to 10 MPa, preferably 0.1 to 2 MPa. A reaction solvent may be used, if necessary, and examples thereof include a nitrile solvent such as acetonitrile and benzonitrile, and a carboxylic acid solvent such as acetic acid and propionic acid.

An optional post-treatment after the oxidation reaction is not particularly restricted, and examples of the post-treatment include a method in which the reaction mixture is filtered to separate the heteropolyacid compound, followed by washing with water and distillation. When the reaction mixture contains a cycloalkyl hydroperoxide corresponding to the cycloalkane as a starting material, the compound can be converted into desired cycloalkanol or cycloalkanone by an alkali treatment, a reduction treatment or the like.

The resulting cycloalkanol can be converted into cycloalkanone by a known method, and cycloalkanone is used as a starting material for producing oxime or lactam.

EXAMPLES

The present invention is described in more detail by following Examples, which should not be construed as a restriction upon the scope of the present invention. Analyses of cyclohexane, cyclohexanone, cyclohexanol and cyclohexyl hydroperoxide in a reaction mixture were conducted by gas chromatography. Based on the results of the analyses, the conversion of cyclohexane, and the respective selectivities to cyclohexanone, cyclohexanol and cyclohexane hydroperoxide were determined.

Reference Example 1

Preparation of Catalyst (a) Preparation of Heteropolyacid Compound:

A 500 ml round bottom flask was charged with 19.8 g (0.06 mol) of sodium tungstate dihydrate and 40 g of water, to prepare an aqueous solution thereof, while stirring at room temperature. After adjusting pH of the aqueous solution to pH 7 by adding 4.1 g of acetic acid, the resulting solution was refluxed with heating. Added dropwise into this refluxed solution over 20 minutes was an aqueous solution of 2.5 g of cobalt (II) acetate tetrahydrate dissolved in 13 g of water, followed by refluxing for additional 15 minutes with heating. The mixture was cooled to room temperature and, after removing precipitated solids by filtration, the filtrate was refluxed again with heating. An aqueous solution prepared by dissolving 13 g of potassium chloride in 25 g of water was added to the refluxed filtrate, and the resulting mixture was continuously refluxed in additional 15 minutes. After cooling the mixture to room temperature, the reaction product was crystallized by maintaining the mixture at 5° C. for 24 hours, and then, 16.6 g of crystals were isolated from the mixture by filtration. The obtained crystal was confirmed to be a potassium salt of Keggin's heteropolyacid $K_7H[Co^{II}W_{11}CO^{II}(H_2O)O_{39}] \cdot 14H_2O$ containing cobalt as a central element and tungsten and cobalt as frame elements, from the results of element analysis, X-ray diffraction analysis, IR spectroscopic analysis and UV-visible spectroscopic analysis.

(b) Purification of Heteropolyacid Compound:

The crystal (3.0 g) of the heteropolyacid salt obtained in the above step (a) was added into 10 ml of a solution in which 0.05 g of acetic acid is dissolved in water. After heating the resulting solution at 100° C., undissolved compounds were removed by filtration to obtain a filtrate. The filtrate was cooled down to room temperature. Further, a saturated aqueous solution (10 ml) of potassium chloride was added to the filtrate, and the product in the filtrate was crystallized by allowing the filtrate to maintain at 5° C. for 24 hours, followed by separating 1.68 g of the crystal by filtration. The crystal obtained was confirmed to be a potassium salt of Keggin's heteropolyacid $K_7H[Co^{II}W_{11}CO^{II}(H_2O)O_{39}] \cdot 14H_2O$ containing cobalt as a central element and tungsten and cobalt as frame elements from the results of element analysis, X-ray diffraction analysis, IR spectroscopic analysis and UV-visible spectroscopic analysis. It was confirmed that the composition and structure of the heteropolyacid salt obtained in the above step (a) was maintained.

(c) Preparation of Hydrotalcite-Like Compound:

Sodium nitrate (18.9 g), sodium hydroxide (10.6 g) and water (82 g) were added in a 500 ml round bottom flask, to prepare an aqueous solution thereof, while stirring at room temperature. An aqueous solution prepared by dissolving 32.7 g of zinc nitrate tetrahydrate and 15.6 g of aluminum nitrate in 63 g of water was added dropwise into the above-prepared aqueous solution at a rate of 60 ml/h. After removing water from the resulting mixture by evaporation at 60° C. over 18 hours, the solid precipitated was separated by filtration. The filtered solid was repeatedly washed with water until the water obtained after the washing exhibits pH 7. The solid was dried at 60° C. for 24 hours to obtain 16.5 g of the solid. The solid was confirmed to be a hydrotalcite-like compound from the result of X-ray diffraction analysis.

(d) Support of Heteropolyacid Compound on Hydrotalcite-Like Compound:

The crystal (2.0 g) of the heteropolyacid salt obtained by repeating the above step (b) several times was added in 74 g of water in a nitrogen atmosphere, and was dissolved by heating at 60° C. The hydrotalcite-like compound (3.9 g) obtained in the above step (c) was added into the solution in a nitrogen atmosphere, to obtain a mixture thereof, while stirring at 60° C. for 22 hours. A solid was separated from the mixture by filtration, and was dried after washing with 27.1 g of water warmed at 60° C., to obtain 3.8 g of a solid. The solid was confirmed to be the heteropolyacid salt supported on the hydrotalcite-like compound from the results of element analysis, X-ray diffraction analysis, IR spectroscopic analysis and UV-visible spectroscopic analysis.

Example 1

A 134 ml autoclave was charged with 34 g (0.40 mol) of a cyclohexane and 0.20 g of the solid obtained in the above step (d) as a catalyst. After increasing the pressure in the autoclave with oxygen, the pressure was adjusted to 0.5 MPa using a back-pressure valve. Then, the temperature in the autoclave was increased to 130° C., while oxygen is circulated, and an reaction was conducted at 130° C. for 24 hours in an oxygen stream. The result of analysis of the reaction solution showed that the conversion of cyclohexane was 5.5%, the selectivity to cyclohexanone was 59.7%, the selectivity to cyclohexanol was 29.1%, and selectivity to cyclohexyl hydroperoxide was 4.1%.

Comparative Example 1

The same procedure as in Example 1 was used, except that the reaction was conducted without using any catalyst. The conversion of cyclohexane was 2.5%, the selectivity to cyclohexanone was 63.1%, the selectivity to cyclohexanonl was 25.7%, and the selectivity to cyclohexyl hydroperoxide was 7.9%.

What is claimed is:

1. A process for producing cycloalkanol and/or cycloalkanone by oxidizing cycloalkane with molecular oxygen in the presence of a heteropolyacid compound comprising a cobalt atom as a central element and a cobalt atom as a frame element.

2. The process according to claim 1, wherein number of cobalt atom as a frame element of the heteropolyacid compound is from 1 to 3.

3. The process according to claim 1, wherein the heteropolyacid compound further comprises at least one of tungsten and molybdenum as a frame element.

4. The process according to claim 1, wherein the heteropolyacid compound is used by being supported on a carrier.

5. The process according to claim 4, wherein the carrier is a hydrotalcite-like compound.

6. The process according to claim 1, wherein cycloalkane is cyclohexane.

* * * * *